Feb. 16, 1960 D. H. MOREY, JR Plant Pat. 1,906
ROSE PLANT
Filed May 13, 1959
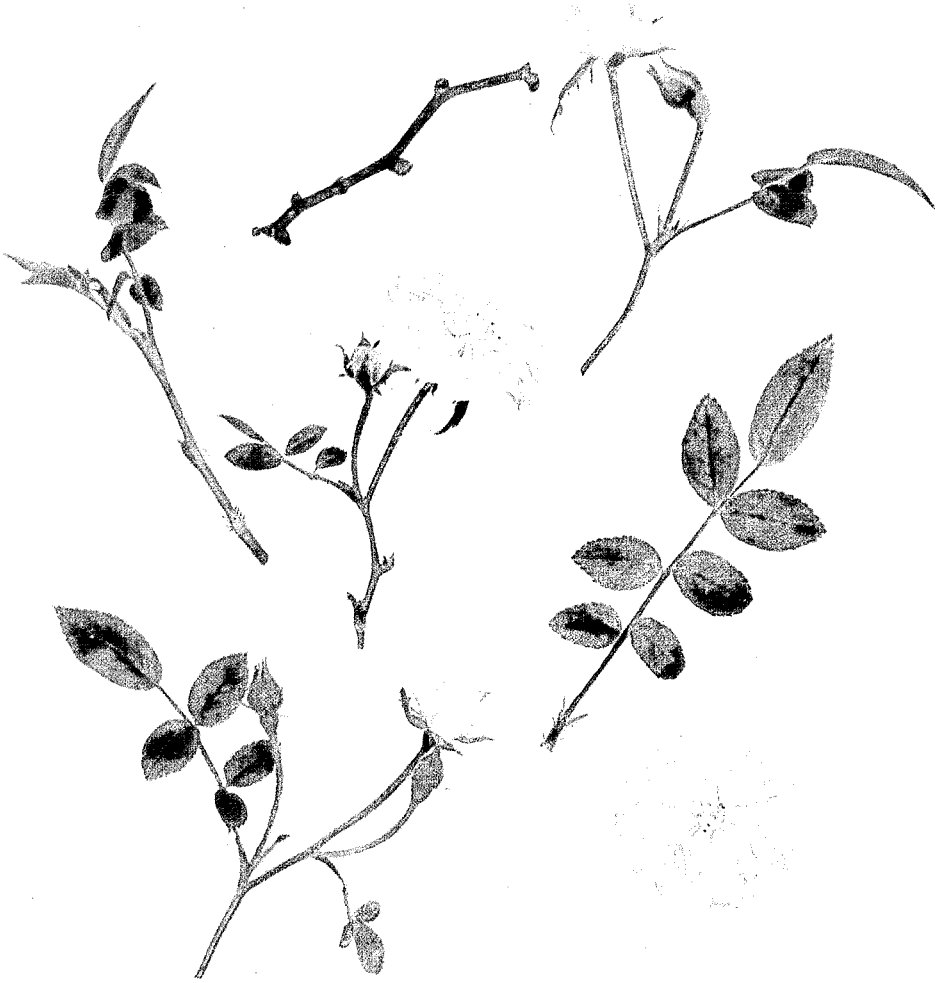
Inventor.
D. H. Morey, Jr.
By: Robb & Robb
Attorneys.

United States Patent Office

Plant Pat. 1,906
Patented Feb. 16, 1960

1,906

ROSE PLANT

Dennison H. Morey, Jr., Pleasanton, Calif., assignor to Jackson & Perkins Company, Newark, N.Y., a corporation of New York Application May 13, 1959, Serial No. 813,049

1 Claim. (Cl. 47—61)

The present invention relates to a new and distinct variety of rose plant of the miniature class, which was originated by me by crossing an unnamed and unpatented sport of "Dick Koster" (unpatented) with the variety "Tom Thumb" (Plant Patent No. 169), said latter variety being known in Europe as "Peon."

The primary objective of this breeding was to produce a new rose variety of the miniature class and having both a low-growing plant habit and a novel flower color which is acceptable for general use. This objective was fully achieved, along with other desirable improvements, as evidenced by the following unique combination of characteristics which are outstanding in the new variety and which distinguish it from its parents, as well as from all other varieties of which I am aware:

(1) An attractive, low-growing, compact plant habit, with the plant averaging from 8 to 10 inches in height;
(2) Ease of propagation by rooted cuttings;
(3) A free-blooming habit;
(4) A miniature flower size averaging from ½ to ¾ inch in diameter, with the flowers of quite double form; and
(5) A distinctive La France Pink, lightly overcast with Rose Pink, general color tonality of the flowers.

Asexual reproduction of the new variety by own-rooted cuttings, as performed at Pleasanton, California and also at Newark, New York, shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed sport of "Dick Koster."
*Pollen parent.*—"Tom Thumb" (known in Europe as "Peon").
Classification:
*Botanic.*—Hybrid chinensis minima.
*Commercial.*—Miniature.

*Flower*

(Observations made from specimens grown in a greenhouse at Newark, New York in the mid-afternoon during the middle of December.)

Blooming habit: Recurrent—continuous.
Bud:
*Size.*—Very small.
*Form.*—Ovoid; is not affected by wet or hot weather.
*Color.*—When sepals first divide—White, Plate 53, lightly overcast with Sea-foam Green, Plate 31.

When petals begin to unfurl—White, Plate 53, lightly overcast with Sea-foam Green, Plate 31, with edge of petal La France Pink, Plate 1. When half-blown; inside of petals—Hermosa Pink, Plate 1, with lower half of petal lightly overcast with White, Plate 53; reverse of petals—White, Plate 53, lightly overcast with Hermosa Pink, Plate 1.
*Sepals.*—Branched; curl back when petals begin to unfurl. Color: inside—Light Cress Green, Plate 31; outside—Jade Green, Plate 31.
*Calyx.*—Color—Rainette Green, Plate 31. Shape—funnel. Size—small. Aspect—smooth. Odor when rubbed—none.
*Peduncle.* — Length — short. Aspect — rough. Strength—erect; slender. Color—Bice Green, Plate 17.
*Opening.*—Opens up well; is not affected by adverse weather conditions.
Bloom:
*Size.*—Small. Average size when fully expanded—from ½ inch to ¾ inch.
*Borne.*—Several together and in irregular clusters; blooms very freely.
*Stems.*—Short; normal strength.
*Form (when first open).*—Open. Permanence—retains its form to the end.
*Petalage.*—Double (full but open center). Number of petals under normal conditions—from 45 to 50.
*Color.*—Center of flower—La France Pink, Plate 1, lightly overcast with White, Plate 53, in the lower half of the petals. Outer petals—Hermosa Pink, Plate 1, lightly overcast with White, Plate 53. Base of petals (aiglet)—Pale Dull Green-Yellow, Plate 17. Inside of petals—La France Pink, Plate 1, lightly overcast with Rose Pink, Plate 12, with the lower half of the petal lightly overcast with White, Plate 53. Reverse of petals—White, Plate 53, lightly overcast with Hermosa Pink, Plate 1. General tonality from a distance—La France Pink, Plate 1, lightly overcast with Rose Pink, Plate 12.
*Discoloration.*—General tonality at end of first day—La France Pink, Plate 1, lightly overcast with Rose Pink, Plate 12. Second day—La France Pink, Plate 1, lightly overcast with Hermosa Pink, Plate 1. Third day—Hermosa Pink, Plate 1, with lower half of the petals lightly overcast with White, Plate 53.
Petals:
*Texture.*—Thin; is not affected by wet or hot weather.
*Appearance.*—Inside—shiny. Outside—shiny.
*Form.*—Oval.
*Arrangement.* — Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—long. As cut flower—long.

*Genital organs*

Stamens, anthers: Small; few; regularly arranged around styles. Color—Empire Yellow, Plate 4.
Stamens, filaments (threads): Short. Color—Pale Greenish Yellow, Plate 5.
Pollen: Color—Baryta Yellow, Plate 4.
Styles: Bunched; even length; short; thin.
Stigmas: Color—Light Green-Yellow, Plate 5.

Ovaries: All enclosed in calyx.
Hips: None.
Seeds: None.

*Plant*

Form: Bush; attains height of from 8 to 10 inches.
Growth: Medium; dwarf; low; compact.
Foliage: Compound of 3 to 7 leaflets.
*Size.*—Small.
*Quantity.*—Normal.
*Color.*—New foliage: upper side—Spinach Green, Plate 5; under side—Biscay Green, Plate 17. Old foliage: upper side—Cress Green, Plate 31. Under side—Light Bice Green, Plate 17.
*Shape.*—Oval pointed.
*Texture.*—Upper side—glossy. Under side—smooth.
*Ribs and veins.*—Ordinary.
*Edge.*—Serrated (saw-toothed).
*Serration.*—Single; small.
*Leaf stem.*—Color—Light Bice Green, Plate 17. Under side—prickly.
*Stipules.*—Medium length; bearded.
Wood:
*New Wood.*—Color—Chromium Green, Plate 32. Bark—smooth.

*Old wood.* — Color — Empire Green, Plate 32. Bark—smooth.
Thorns:
*Thorns.*—Quantity: on main stalks from base—few; on laterals from stalk—few. Form—narrow base; short; straight. Color (when young)—Light Bice Green, Plate 17. Position—irregular.
*Prickles.*—Quantity: on main stalks—none; on laterals—none.
*Short needles.*—Quantity: on main stalks—none; on laterals—none.

I claim:

A new and distinct variety of rose plant of the miniature class, substantially as herein shown and described, characterized particularly as to novelty by the unique combination of an attractive, low and compact plant habit, ease of propagation by rooted cuttings, a free-blooming habit, miniature flower size of quite double form, and a distinctive La France Pink, lightly overcast with Rose Pink general color tonality of the flowers.

No references cited.